United States Patent
Redel et al.

(10) Patent No.: US 7,945,082 B2
(45) Date of Patent: May 17, 2011

(54) ANALYSIS METHOD FOR DATA OF AN EXAMINATION OBJECT, FEATURING CORRELATION OF A VOLUME DATA RECORD WITH A NUMBER OF PROJECTION IMAGES

(75) Inventors: Thomas Redel, Poxdorf (DE); Estelle Camus, Mountain View, CA (US)

(73) Assignee: Siemens Aktiengesellschaft, Munich (DE)

( * ) Notice: Subject to any disclaimer, the term of this patent is extended or adjusted under 35 U.S.C. 154(b) by 836 days.

(21) Appl. No.: 11/973,246

(22) Filed: Oct. 5, 2007

(65) Prior Publication Data

US 2008/0095423 A1    Apr. 24, 2008

(30) Foreign Application Priority Data

Oct. 23, 2006    (DE) .................... 10 2006 049 865

(51) Int. Cl.
  *G06K 9/00*    (2006.01)
  *A61B 5/05*    (2006.01)
(52) U.S. Cl. .................... 382/131; 382/285; 600/410
(58) Field of Classification Search .................. 382/128, 382/129, 130, 131, 132, 133, 134, 154, 162, 382/168, 173, 181, 190, 194, 196, 199, 232, 382/254, 274, 276, 285–289, 294, 296, 305, 382/312; 378/21, 62; 600/407, 410
See application file for complete search history.

(56) References Cited

U.S. PATENT DOCUMENTS

| | | | | |
|---|---|---|---|---|
| 5,602,891 A | * | 2/1997 | Pearlman | 378/62 |
| 6,292,683 B1 | * | 9/2001 | Gupta et al. | 600/410 |
| 7,444,011 B2 | * | 10/2008 | Pan et al. | 382/131 |
| 7,693,563 B2 | * | 4/2010 | Suresh et al. | 600/407 |
| 2006/0078183 A1 | * | 4/2006 | deCharms | 382/128 |
| 2006/0235288 A1 | * | 10/2006 | Lavi | 600/407 |
| 2007/0036418 A1 | * | 2/2007 | Pan et al. | 382/131 |

OTHER PUBLICATIONS

Hrvoje Bogunovic and Sven Loncaric; "Estimating Perfusion Using X-Ray Angiography"; Proceedings of the 4th International Symposium on Image and Signal Processing and Analysis, 2005, pp. 147-150.*
Horst Traupe; "CME Radiologie—Zerebrale Perfusion"; Jan. 1, 2004; pp. 1-18; Schering, Thieme.
Matthias König; "CT-Perfusionsbildgebung bei zerebraler Ischämie"; Radiologie Update Feb. 2001; pp. 187-202.
K.A. Miles, M.R. Griffiths; "Perfusion CT: a worthwhile enhancement?"; the British Journal of Radiology; Apr. 2003; pp. 220-231.

(Continued)

*Primary Examiner* — Seyed Azarian

(57) ABSTRACT

Data of an examination object comprises a volume-data record and a plurality of two-dimensional projection images. The volume-data record includes voxels where each voxel is assigned to a location in three-dimensional space. Each projection image includes pixels where each pixel is assigned to a location in a two-dimensional-projection plane and has a value. Each pixel is assigned a projection volume, this being specified in that it is mapped by the radioscopy onto the pixel to which it is assigned. A sub-volume of the volume-data record is selected. The projection images are registered in relation to the volume-data record. A functional parameter of the examination object is specified for the pixels of the projection images, depending on their values. For each pixel, when specifying the functional parameter, consideration is given to the locations and/or the number of those voxels which are positioned both within the sub-volume and within the projection volume.

11 Claims, 7 Drawing Sheets

OTHER PUBLICATIONS

Patrick Kurp; "AXIOM Artis FD Systems—DynaCT—A Breakthrough in Interventional 3D Imaging"; Siemens Medical; Jan. 2005; pp. 46-51.

Hrvoje Bogunović and Sven Lončarić; "Estimating Perfusion Using X-Ray Angiography"; Proceedings of the 4<sup>th</sup> International Symposium on Image and Signal Processing and Analysis, 2005, pp. 147-150.

T.P.L. Roberts et al; "Integrating X-ray antiography and MRI for endovascular interventions"; Nov. 2000, Medica Mundi 44/3, pp. 2-9.

* cited by examiner

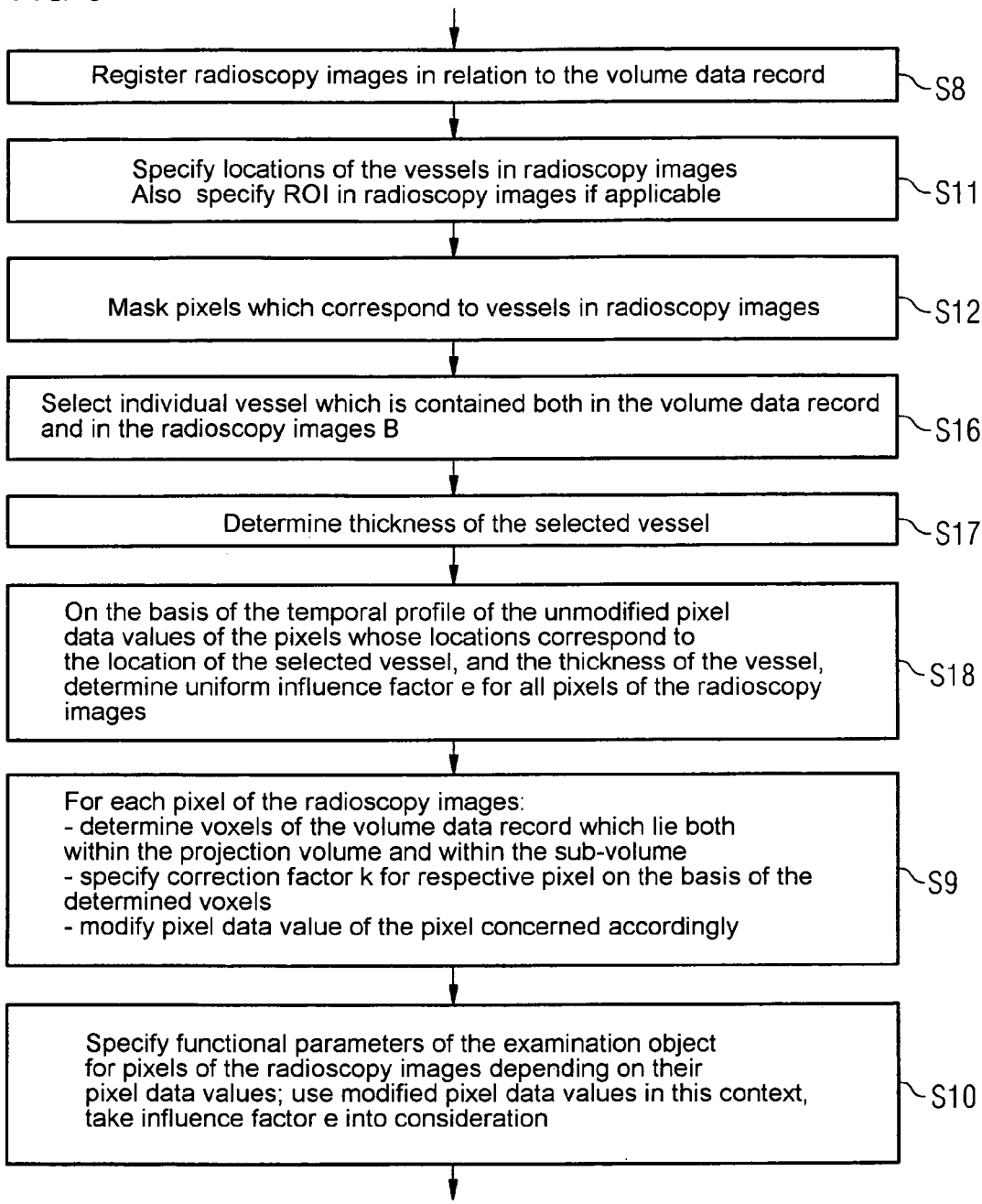

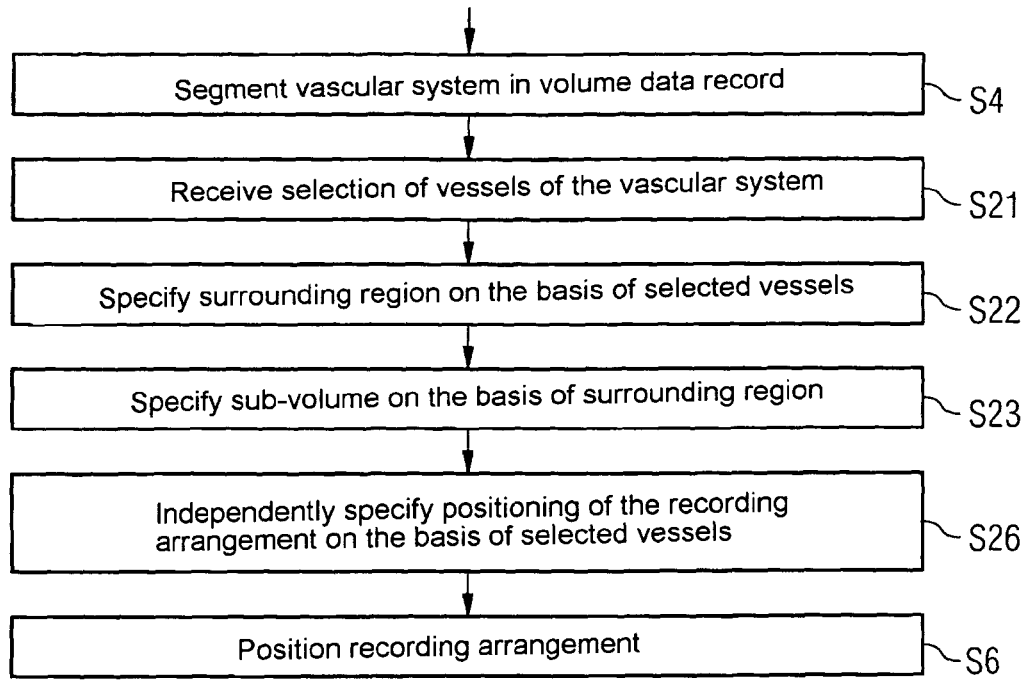
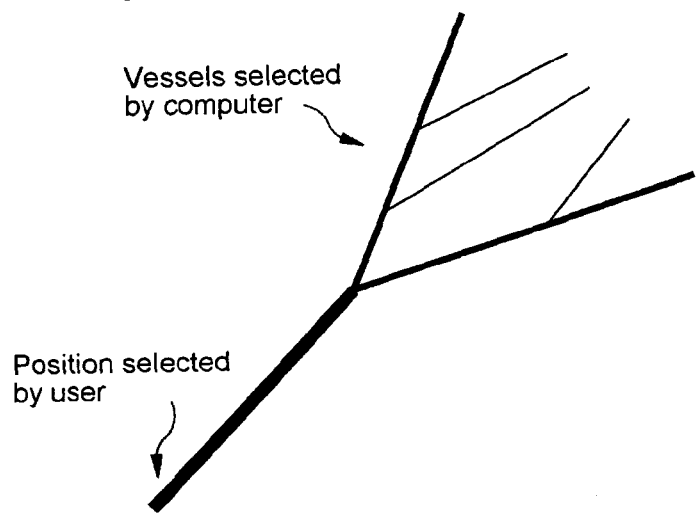

ANALYSIS METHOD FOR DATA OF AN EXAMINATION OBJECT, FEATURING CORRELATION OF A VOLUME DATA RECORD WITH A NUMBER OF PROJECTION IMAGES

CROSS REFERENCE TO RELATED APPLICATIONS

This application claims priority of German application No. 102006049865.8 DE filed Oct. 23, 2006, which is incorporated by reference herein in its entirety.

FIELD OF INVENTION

The present invention relates to an analysis method for data of an examination object. Such analysis methods are generally known. In particular, analysis methods are known in which the data of the examination object comprises a volume data record of the examination object and/or a number of two-dimensional projection images of the examination object. Purely by way of example, a 3D angiography is cited in relation to the analysis of a volume data record, and a perfusion analysis is cited in relation to the analysis of a number of two-dimensional projection images. The present invention relates to such analyses.

BACKGROUND OF INVENTION

For image-based diagnosis of e.g. cerebral illnesses such as stroke, AVM (arterial-vascular malformation) or cancer-related illnesses, the established methods such as CT (computer tomography), MR (magnetic resonance) and also C-arm-based 3D imaging are available today. In relation to CT and MR, for example, reference is made to the brochure "CME Radiologie—Zerebrale Perfusion" by Horst Traupe, Schering and Thieme, 2005. This analysis method includes the analysis of a volume data record which features a multiplicity of voxels, wherein each voxel is assigned to a location in the three-dimensional (3D) space. A common feature of these techniques is that they supply morphological information about the examination object.

The prior art also discloses all variety of techniques which provide functional information about the examination object in the field of CT and MR imaging. With regard to the blood supply of the examination object, in particular, it is possible to determine its perfusion, the volume of blood contained, the so-called "mean transit time" and other parametric variables. Important information can be derived from the comparison between the various variables. Reference is made, for example, to the specialist article "CT-Perfusionsbildgebung bei zerebraler Ischämie" by Matthias König, Radiologie up2date 2/2001, pages 187 to 202, and to the specialist article "Perfusion CT: a worthwhile enhancement?" by K. A. Miles and M. R. Griffiths, The British Journal of Radiology, April 2003, pages 220 to 231.

The imaging techniques are generally used in a pre-intervention phase. Consequently, they are not available during a therapeutic intervention. Interventions are generally carried out in the angiography laboratory, which usually includes a C-arm-based x-ray system. Such x-ray systems make it possible to generate morphological images in the three-dimensional space, and also in principle to perform functional measurements. Reference is made to the reprint "AXIOM Artis FD Systems—DynaCT—A Breakthrough in Interventional 3D Imaging" by Patrick Kurp, originally published in Medical Solutions, January 2005, pages 46 to 51.

The generation of three-dimensional morphological images and also the taking of functional measurements are admittedly possible in principle using angiography facilities. As a result of the limited rotation speed and the associated limited temporal resolutions, however, the applicability is only restricted. Furthermore, a high radiation dose is applied, thereby strictly limiting the repeated use.

One possibility for overcoming the limited temporal resolution while nonetheless achieving a high spatial resolution is the use of scenes from projection recordings, preferably in the DSA mode (DSA=digital subtraction angiography). For example, reference is made to the specialist article "Estimating Perfusion Using X-Ray Angiography" by Hrvoje Bogunović and Sven Lončarić, published in Proceedings of the 4th International Symposium on Image and Signal Processing and Analysis, 2005, pages 147 to 150. The projection recordings correspond to projection images featuring a multiplicity of pixels, wherein each pixel is assigned to a location in a two-dimensional projection plane and has a pixel data value. In this specialist article, an approach is described for qualitatively calculating and displaying perfusion-correlated parameters. The specification of the functional parameters of the examination object takes place for the pixels of the projection recordings depending on their pixel data values. The solution offered in the cited specialist article is firstly nonetheless subject to limitations, which could be removed in principle by the elimination of vessels. However, a means of eliminating vessels is not specified in the specialist article. Secondly, as a result of the projective nature of the recordings and the typical geometry of the examination objects, different organ paths are traversed by the x-rays which are used there and hence depending on the location in the image—variously large volumes of the examination object are observed. Without taking into consideration the observed volume in each case, the quantitative analysis therefore varies from pixel to pixel.

The specialist article "Integrating X-ray angiography and MRI for endovascular interventions" by T. P. L. Roberts et al., MEDICA MUNDI 44/3, November 2000, pages 2 to 9, discloses an analysis method for data of an examination object, wherein the data comprises at least one volume data record of the examination object and a number of two-dimensional projection images of the examination object. The volume data record features a multiplicity of voxels. Each voxel is assigned to a location in the three-dimensional space. Each projection image features a multiplicity of pixels. Each pixel is assigned to a location in a two-dimensional projection plane. It features a pixel data value in each case. The projection images are registered in relation to the volume data record. Depending on their pixel data values, at least one functional parameter of the examination object is specified for the pixels of the projection images.

SUMMARY OF INVENTION

The present invention addresses the problem of providing possibilities for carrying out quantitative analyses of a number of two-dimensional projection images of the examination object, said analyses being uniform for each pixel and therefore comparable from pixel to pixel.

According to the invention, the data to be analyzed of the examination object comprises at least one volume data record and a number of projection images. A projection volume is assigned to each pixel of the projection images, wherein the projection volumes are specified such that, by means of the radioscopy, they are mapped onto the pixels to which they are assigned in each case. A sub-volume of the volume data record is selected. The projection images are registered in relation to the volume data record. At least one functional parameter of the examination object is specified for the pixels of the projection images, depending on their pixel data values. For each pixel, when specifying the at least one functional parameter, consideration is given to the locations and/or the number of those voxels which are positioned both within the sub-volume and within the projection volume that is assigned to the pixel concerned.

Using this approach, it is possible to normalize the projection images in terms of pixels, such that comparable quantitative analyses are possible following the normalization, said analyses being similar to those already known for 3D data records, e.g. from the above-cited specialist article "CT-Perfusionsbildgebung bei zerebraler Ischämie" by Matthias König, for CT sectional images and the like.

The examination object usually contains a vascular system including vessels and the associated environment. In a preferred embodiment, at least locations of segmented vessels are specified in the projection images. As a result of this, it is possible that the pixels corresponding to the segmented vessels are not taken onto consideration when specifying the at least one functional parameter. The quality of the analysis can be increased as a result of this approach.

Alternatively or additionally, on the basis of the pixel data values of pixels corresponding to the segmented vessels, it is possible to determine a uniform factor of influence for all pixels of the projection images, said factor being used in the specification of the at least one functional parameter. Using this approach, it is possible to quantify the effect of e.g. a contrast medium which is supplied to the vascular system.

In principle, it is possible to specify the sub-volume in an ad-hoc manner. For example, a user can preset points in the volume data record, thereby determining a convex envelope which contains all preset points. However, the vascular system is preferably segmented in the volume data record, and some of the segmented vessels are selected. In this case, the sub-volume is specified on the basis of the selected segmented vessels.

The projection images are preferably captured in the volume data record after the selection of the segmented vessels. In this case, it is possible to specify a positioning of a recording arrangement, by means of which the projection images are captured, depending on which of the segmented vessels were selected.

The projection images can be so-called native images in individual cases. However, each projection image is usually determined as a DSA image of a corresponding basic image and a reference image.

In principle, the volume data record can be determined in any chosen manner. It is crucial only that it is available. However, the volume data record is preferably determined on the basis of further projection images, wherein the further projection images are captured by means of the same recording arrangement as is also used for capturing the projection images whose pixel data values are analyzed for the purpose of specifying the at least one functional parameter.

BRIEF DESCRIPTION OF THE DRAWINGS

Further advantages and details are revealed from the following description of exemplary embodiments in conjunction with the drawings. In the form of a schematic representation:

FIGS. 8 and 9 show flow diagrams,

FIGS. 10 and 11 show projections of the volume data record, and

DETAILED DESCRIPTION OF INVENTION

Figure 1:
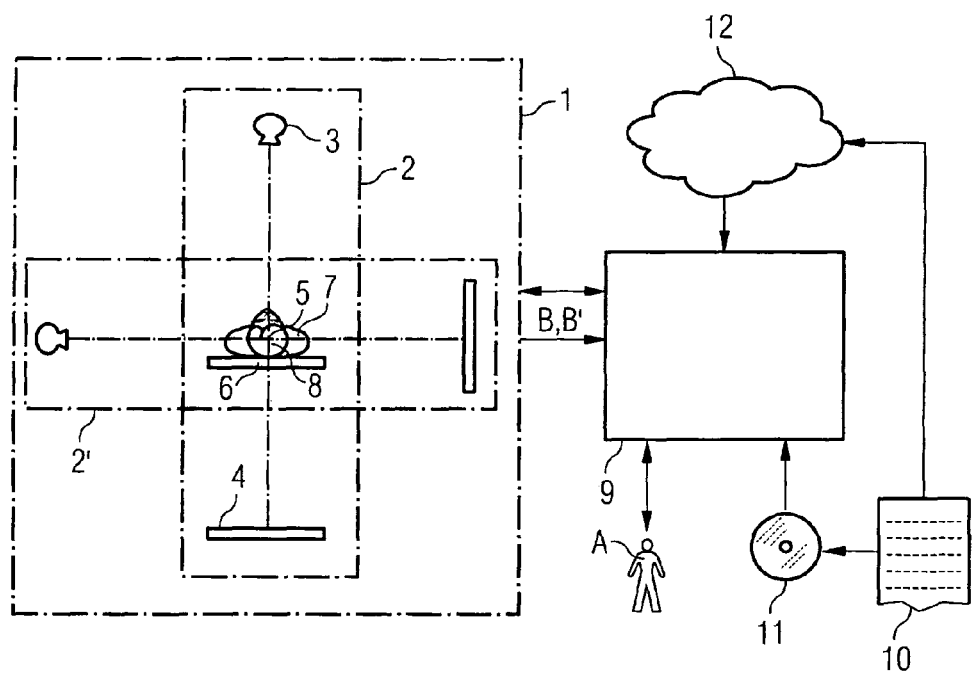
FIG. 1 shows a radioscopy device and a control device for this.

In accordance with FIG. 1, a radioscopy device 1 features a recording arrangement 2. The recording arrangement 2 features a radiation source 3 and a radiation detector 4. The radiation source 3 and the radiation detector 4 can usually be swiveled about a swiveling axis 5, and specifically such that they are always situated diametrically opposite to each other in relation to the swiveling axis 5. The radiation detector 4 is normally two-dimensional, i.e. having the form of a surface detector.

One example of a radioscopy device 1 as per FIG. 1 is an angiography facility. This can be designed as a C-arm facility, or preferably as a facility having a robotic carrier platform.

A patient 7 is arranged in the vicinity of the swiveling axis 5, e.g. on a patient bed 6. The patient 7—or more precisely a part of the patient 7, e.g. the brain of the patient 7—is the examination object 8 in the present case.

The radioscopy device 1 is controlled by a control device 9. The control device 9 effects inter alia
- the positioning of the recording arrangement 2,
- the activation of the radiation source 3, such that it emits radiation which penetrates examination object 8,
- the reading of the radiation detector 4, such that projection images B are captured, and
- the positioning of the patient bed 6.

The projection images B, which are captured by the radiation detector 4, are initially supplied to the control device 9. No editing of the projection images B takes place in the context of the control of the radioscopy device 1. The projection images B must nonetheless be edited and analyzed. A computer which has a data link to the control device 9 is generally provided for this purpose. In this case, the control device 9 transfers the projection images B captured by the radiation detector 4 to the computer, which then undertakes the further analysis and editing. Alternatively, however, it is possible for the control device 9 to be integrated in the computer. This last-cited embodiment is illustrated in FIG. 1. In this case, the computer is also designed as a control device 9 for the radioscopy device 1. The terms "computer" and "control device" are therefore used synonymously in the following. The same reference sign 9 is also used for both elements.

The operation of the computer 9 is determined by a computer program 10 which is supplied to the computer 9 via a data medium 11 (e.g. a CD-ROM or a USB memory stick) or a network link 12 (e.g. the Internet) and is stored in the computer 9. The computer program 10 features a sequence of machine instructions 13. The sequence of machine instructions 13 can be executed by the computer 9. Its execution causes the computer 9 to operate the radioscopy device 1 correctly in its capacity as control device for the radioscopy device 1. The running of the sequence of machine instructions 13 also causes the computer 9, in its capacity as analysis device for the projection images B, to execute an analysis method which is explained in detail below.

As a result of the programming in the computer program 10, the radioscopy device 1 can usually be operated in various ways. The analysis of the projection images B in various ways is also usually possible. To the extent that these operating modes and analysis possibilities are already disclosed in the prior art, they can also remain appropriate. However, the operating and analysis possibilities described below in connection with the FIGS. 2 to 12 are also appropriate. In this context, it is noted that the order of steps which are mentioned and described below in connection with the FIGS. 2 to 12 need only be retained if these steps are necessarily constructed one upon the other. Otherwise, the order can also be changed.

Figure 2:
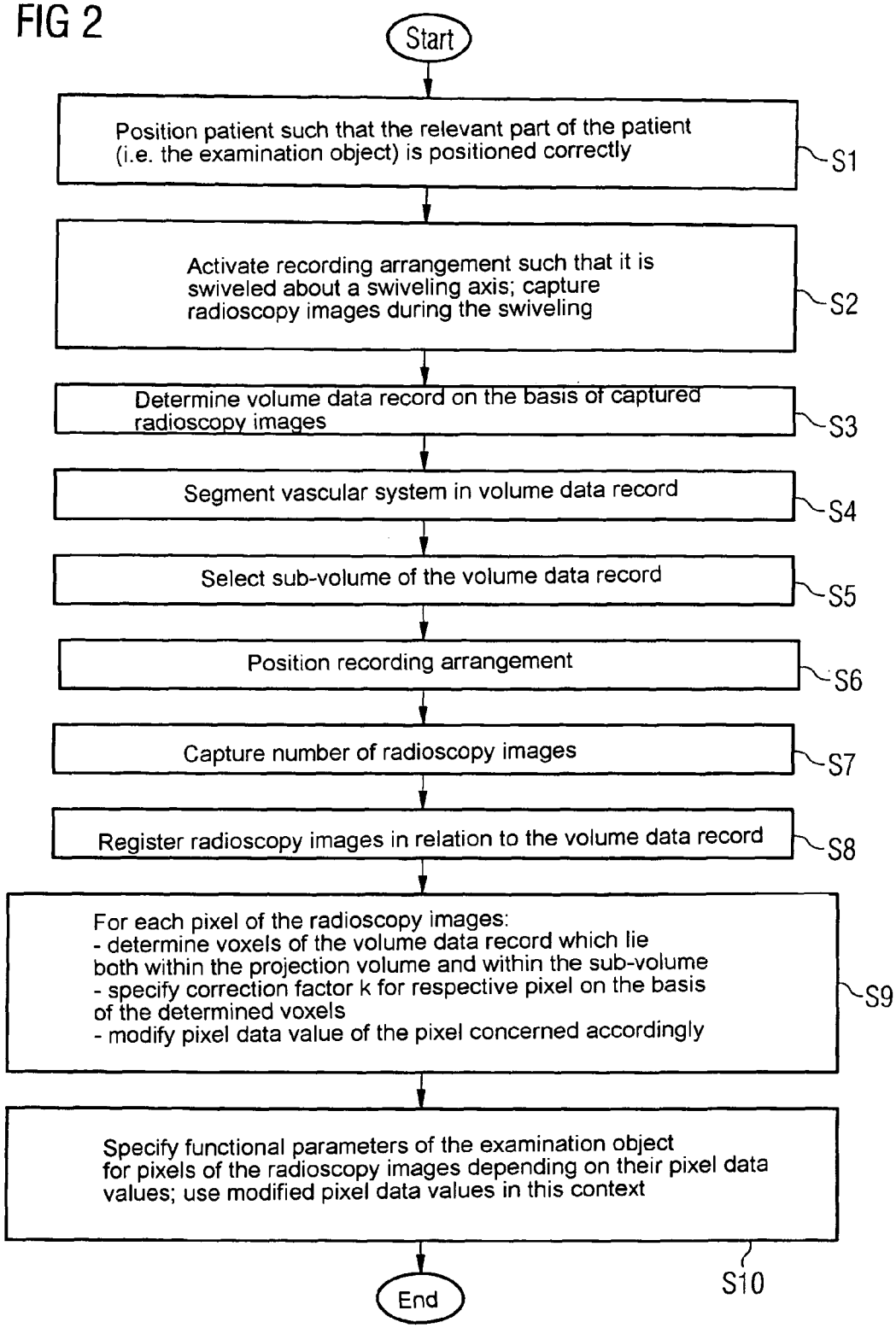
FIG. 2 shows a flow diagram.
Figure 3:
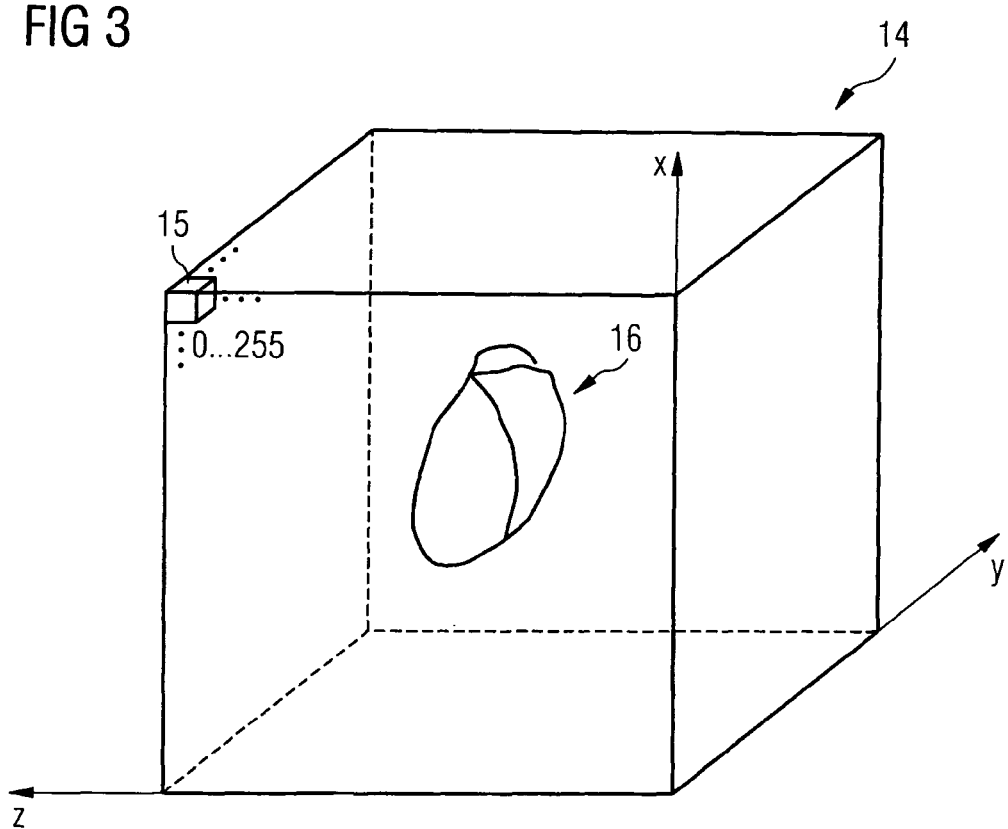
FIG. 3 shows a possible representation of a volume data record.

In accordance with FIG. 2, in a step S1 the patient 7 is first positioned such that the relevant part of the patient 7 (i.e. the examination object 8 within the sense of the present invention) is correctly positioned. The correct positioning is generally established when the swiveling axis 5 is central in the examination object 8.

The step S1 is usually carried out partly by direct human intervention and partly by the control device 9. In particular, the positioning of the patient 7 on the patient bed 6 is usually performed by human intervention, either by the patient 7 or by others. However, the positioning of the patient bed 6 is usually performed via corresponding activation by means of the control device 9.

In the context of the present invention, a volume data record 14 of the examination object 8 is required. The volume data record 14 can be generated and supplied to the computer 9 by any means. However, it is preferred if the volume data record 14 is determined by means of further projection images B' which are captured by the radioscopy device 1. For this purpose, in a step S2 the control device 9 activates the recording arrangement such that this is swiveled about the swiveling axis 5 and, during the swiveling, the further projection images B' are captured by the radiation detector 4 and supplied to the control device 9. In a step S3, the computer 9 thereupon determines volume data record 14. The computer 9 preferably carries out the steps S2 and S3 automatically, as soon as it has received a corresponding start command from a user A.

The volume data record 14 (see FIG. 3) includes a multiplicity of voxels (=volume elements) 15. Each voxel 15 is assigned to a location in the three-dimensional space. It has a volume data value. The volume data value is usually an 8-bit value. It can therefore have the values 0, 1, 2, ... 255, for example. However, other bit lengths (e.g. 4 bits or 12 bits) are also conceivable. The location in the space can be specified e.g. by three spatial coordinates x, y, z, which can have the values 0, 1, 2, ... 1023, these being independent of each other. The spatial coordinates x, y, z are usually the coordinates of a right-angled Cartesian coordinate system.

As mentioned previously, the examination object 8 can be the brain of the patient 7, for example. In this case, it naturally contains the brain mass itself, but also inter alia a system of blood vessels via which the brain mass is supplied with blood. Furthermore, the brain is surrounded by other tissue (in particular the cranial bone). In a step S4, the vascular system is segmented in the volume data record 14 by the computer 9, preferably independently. Segmentation methods per se are generally known, and hence there is no need to discuss the segmentation in greater detail at this point.

In a step S5, a sub-volume 16 of the volume data record 14 is selected. The selection of the sub-volume 16 is preferably done by the user A, wherein the computer 9 supports the user A, preferably interactively. For example, the user A can select a vessel branch in the volume data record 14 and the computer 9 can independently specify the sub-volume 16 on the basis of the selected vessel branch. The step S5 is explained in greater detail further below.

In a step S6, the control device 9 then positions the recording arrangement 2 again. This positioning is preferably retained in the context of the further method.

If the radioscopy device 1 features a further recording arrangement 2' (marked by means of a broken line in FIG. 1), and the radioscopy device 1 is therefore designed as a biplane facility, the further recording arrangement 2' can be positioned in conjunction with the first cited recording arrangement 2 such that the two recording arrangements 2, 2' feature ray paths which are at least essentially orthogonal relative to each other.

In a step S7, the control device 9 captures a number of projection images B by means of the radiation detector 4. The step S7 is preferably carried out completely automatically by the computer 9. The projection images B are captured consecutively relative to time, the positioning of the recording arrangement 2 remaining essentially constant. They therefore form a temporal sequence (scene). The temporal sequence of the projection images B shows, for example, the dissemination of a contrast medium in the vessels and in the tissue surrounding the vessels, and optionally the rinsing out of the contrast medium from the tissue. Any application of the contrast medium that may be necessary, in particular by means of intra-arterial injection, is not itself part of the analysis method according to the invention.

With the exception of detector-specific error correction, image-processing algorithms should not be used during the capture of the scene if possible. The recording conditions (e.g. operating voltage and operating current of the x-ray source if such is used as a radiation source 3, clocking of the radiation detector 4, etc.) should also be kept as constant as possible. The settings of the recording conditions can be stored, for example, in a special organ program of the control device 9, which program guides the user A through the complete routine of FIG. 2. The organ program can also contain, for example, preferred projection parameters (angulations) and set these in a semi-automatic (i.e. requiring only confirmation from the user A) or fully automatic manner as required.

Figure 4:
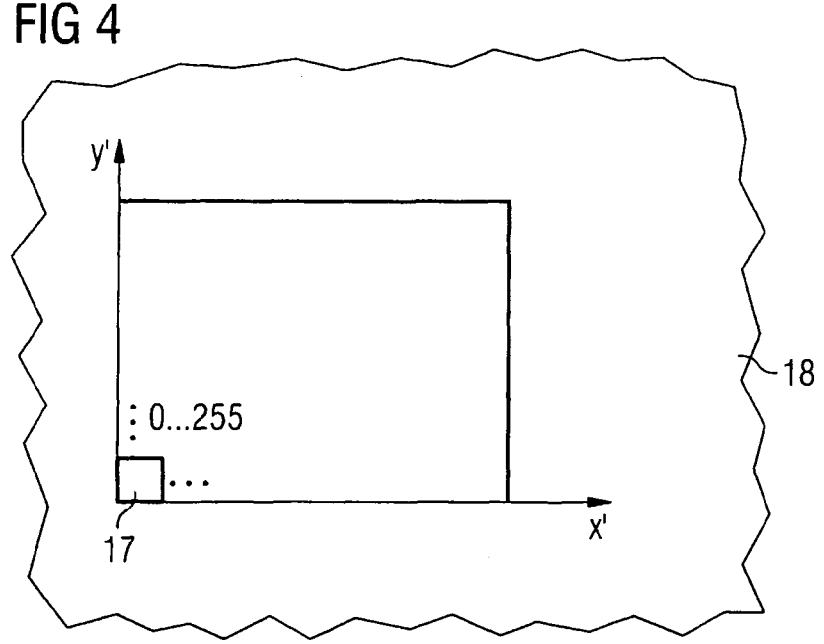
FIG. 4 shows a possible mapping geometry.

Each projection image B features a number of pixels (picture elements) 17; see FIG. 4. Each pixel 17 is assigned to a location in a two-dimensional projection plane 18. The location can be specified e.g. by means of two area coordinates x', y' which can independently take the values 0, 1, 2, ... 1023. Each pixel 17 has a pixel data value which lies between 0 and 255 in the case of a typical bit length of 8 bits.

Figure 5:
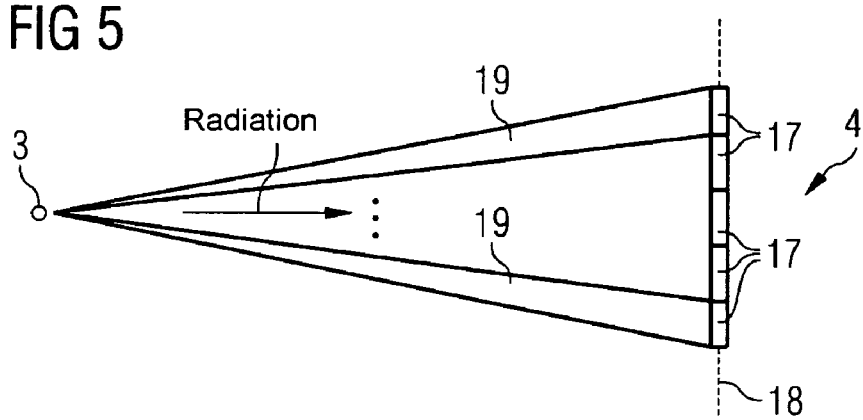
FIGS. 5 to 7 show mapping geometries with projection volumes.
Figure 6:
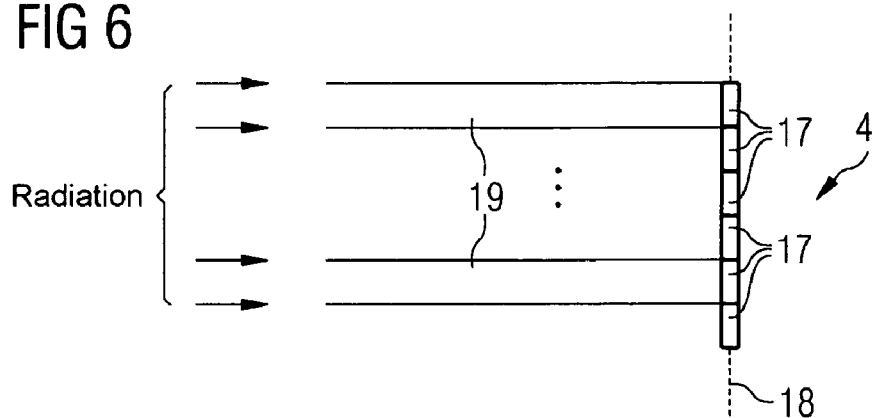
Figure 7:
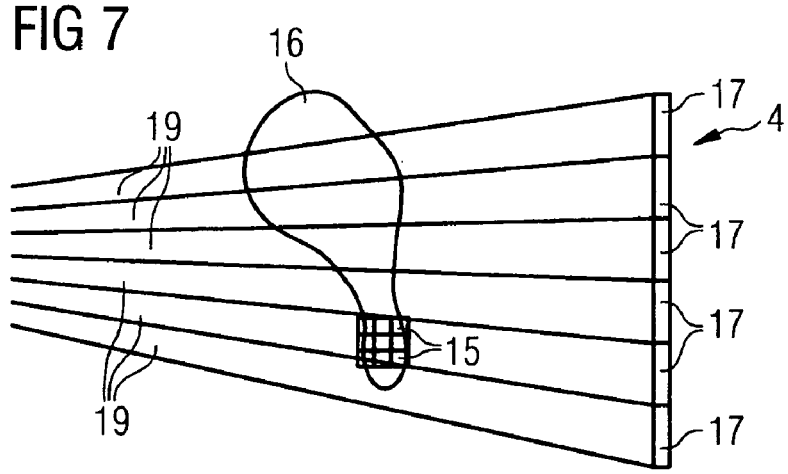
Figure 11:
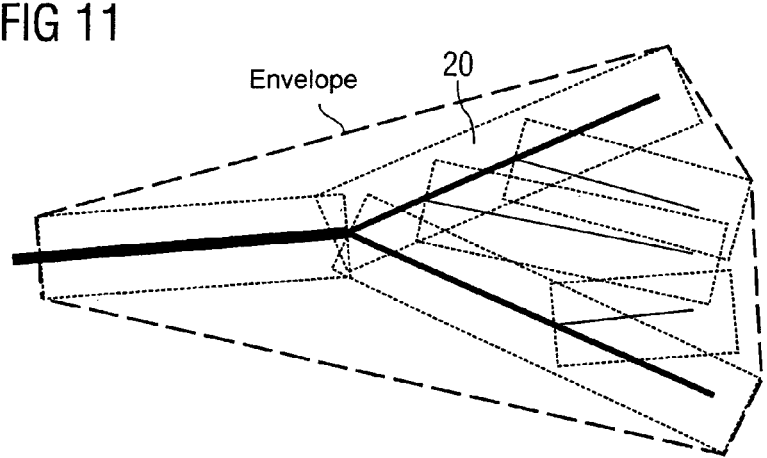

A projection volume 19 is assigned to each pixel 17; see FIGS. 5 and 6. The projection volumes 19 are specified in that they are mapped onto the pixels 17 as a result of the radioscopy of the examination object 8. In this context, each projection volume 19 is mapped onto the pixel 17 to which it is assigned. The projection volumes 19 are derived from the geometry and the positioning of the recording arrangement 2. By way of example, FIG. 5 shows two projection volumes 19 for the case of a perspective projection and FIG. 6 shows two projection volumes 19 for the case of a parallel projection.

In a step S8, the projection images B are registered in relation to the volume data record 14. The registration of projection images B relative to a volume data record 14 is known per se, and therefore need not be explained. To the extent that it is possible and necessary (e.g. due to slight image movements, the projection images B can also be registered relative to each other in the context of the step S8. The step S8 is preferably performed fully automatically by the computer or interactively by the user 1.

In the present case, the volume data record 14 was determined on the basis of a number of further projection images B', wherein the further projection images B' for determining the volume data record and the projection images B of the scene were captured by means of the same recording arrangement 2. This approach is particularly advantageous because the registration is simpler. In particular, the registration can be determined fully automatically from the positioning of the recording arrangement 2 in the step S6, if the examination object 8 is not moved between the steps S1 and S7.

By virtue of the registration, the situation of the projection plane 18 and the virtual position of the radiation detector 4 and the virtual mapping geometry are known in the volume data record 14. By virtue of the registration of the projection images B in relation to the volume data record 14, for each pixel 17 of the projection images B its assigned projection volume 19 can therefore also be mapped in the volume data record 14 and sectioned using the selected sub-volume 16; see FIG. 7. Consequently, in a step S9, for each pixel 17 of the projection images B, it is possible to determine those voxels 15 of the volume data record 14 which lie both within the projection volume 19 which is assigned to the relevant pixel 17 and within the sub-volume 16. In step S9, a correction factor k can then be specified for the relevant pixel 17 of the projection images B, and the pixel data value of the relevant pixel 17 is modified on the basis of said correction factor k. The step S9 is preferably performed fully automatically by the computer 9.

In order to determine the correction factor k, in the simplest case, provision is made merely for determining the number of voxels contained in the section of the sub-volume 16 and of the relevant projection volume 19. In a first approximation, the number is seen as proportional to the local thickness of the sub-volume 16 (in the projection direction). In a first approximation, therefore, the local thickness of the sub-volume 16 can also be used for determining the correction factor k. This last-cited approach is advantageous in particular in the case of a parallel projection (see FIG. 6). However, it also produces significantly better results in the case of a perspective projection (see FIG. 5). The inclusion of the local thickness of the sub-volume 16 in the specification of the correction factor k can be linear (in particular in the case of a parallel projection) or greater than linear (in particular in the case of a perspective projection).

Alternatively, in addition to the number of voxels 15, the location of the voxels 15 within the mapping geometry can also be taken into consideration. This approach can be advantageous in particular in the case of perspective projections.

In a step S10, the computer 9 specifies at least one functional parameter of the examination object 8 for the pixels 17 of the projection images B depending on their pixel data values. For example, the computer 9 can specify the perfusion or the TIMI blush grade, the mean transit time, the blood volume, etc. The computer 9 preferably executes the step S10 fully automatically. However, for the purpose of specifying the above-mentioned functional parameters—and also for the purpose of specifying other functional parameters—the computer 9 preferably does not use the original pixel data values of the projection images B, but instead uses the pixel data values which were modified in accordance with the step S9. As a result of this modification, the pixel data values are normalized such that not only qualitative but also quantitative analyses of the projection images B can be performed correctly. Previously it was only possible correctly to provide such quantitative information output in the case of three-dimensional volume data records (more precisely: sequences of volume data records).

After the functional parameters have been determined, it is obviously possible to depict determination results visually. This step is known per se and remains unchanged in comparison with the prior art. Therefore no further details are provided in relation to this step.

In connection with FIGS. 8 to 12, a number of modifications and additions to the method in FIG. 2 are explained below, thereby allowing optimization of the approach in FIG. 2. In principle, the individual modifications and additions can be realized independently of each other, provided they are not inevitably constructed one upon the other. They can also be combined with each other if required, provided they are not automatically mutually exclusive.

In accordance with FIG. 8, steps S11 and S12 can be inserted between the steps S8 and S10. In this context, the steps S11 and S12 can be inserted before the step S9 in accordance with FIG. 8. Alternatively, however, they could also be inserted after the step S9.

In the step S11, in the projection images B, the computer 9 specifies the locations of the vessels in the projection images B. The computer 9 preferably executes the step S11 fully automatically.

On the basis of the temporal profile of the modified or unmodified pixel data values, it is e.g. possible to decide, per pixel 17 or per group of pixels 17, whether the type "vessel", the type "background" or the type "perfusion" is assigned to the relevant pixel 17 or to the group of pixels 17 concerned. Such approaches are explained in detail in, for example, the earlier applications 10 2005 039 189.3, 10 2006 025 422.8 and 10 2006 025 423.6 of the applicant.

Alternatively, in the context of the step S11, the vessels which were segmented in the step S4 of FIG. 2 can be e.g. mapped onto the projection images B. This mapping is possible because the projection images B are registered in relation to the volume data record 14 (compare step S8 of FIGS. 2 and 8). In many cases, the mapping of the vessels onto the projection images B can be limited to vessels which lie in the selected sub-volume 16, or which would lie in the selected sub-volume 16 before a possible masking of the vessels from the selected sub-volume 16, or which are at a distance which lies below a maximal distance relative to the selected sub-volume 16. It is also possible to use other desired techniques for segmenting the vessels in the projection images B.

In the context of the step S11, it is also possible to specify an ROI (=region of interest) in the projection images B, e.g. by mapping the sub-volume 16 as a whole. In this way, other non-relevant regions of the projection images B (in particular background, i.e. non-perfused regions) can be excluded from the analysis if applicable.

In the step S12, the pixels 17 which correspond to the vessels are masked in the projection images B. These pixels 17 are therefore no longer taken into consideration in the context of the step S10. The step S12 is likewise preferably executed fully automatically by the computer 9.

It is alternatively or additionally possible to combine the step S11 with the steps S16 to S18 as per FIG. 8. The step S12 can be omitted in this case, though it can alternatively remain present.

In the step S16, an individual vessel is selected which is contained in both the volume data record 14 and the projection images B. The selection can be made on the basis of a user input, for example. A vessel is preferably selected which runs essentially parallel with the projection plane 18 of the projection images B and has a maximal thickness in the direction of the projection plane 18. The location of the selected vessel in the projection images B is marked.

In the step S17, the thickness of the vessel which was selected in the step S16 is determined. In the step S18, an influence factor e is determined on the basis of the temporal profile of the unmodified pixel data values of the pixels 17 whose locations correspond to the location of the selected vessel, and the thickness of the vessel. The influence factor e is taken into consideration in the context of the step S10 when specifying the at least one functional parameter. It is the same for all pixels 17 of the projection images B. The computer 9 preferable executes the steps S17 and S18 fully automatically.

As mentioned above in connection with the step S5, the positioning of the recording arrangement 2 for capturing the sequence of projection images B is usually only determined after the selection of the sub-volume 16. Furthermore, the sub-volume 16 can be determined on the basis of the vascular system or on the basis of the selected vessels. This is explained in further detail in connection with the FIGS. 9 to 11.

In accordance with FIG. 9, the step S5 can be divided into steps S21 to S23. In the step S21, the computer 9 receives a selection of vessels of the vascular system. For example, a position of a vessel can be preset for the computer 9 by the user A in the volume data record 14; see FIG. 10. If the flow direction of the blood in the vascular system is known, and this is generally the case, the computer 9 can e.g. independently select all subsequent vessels in the flow direction. Alternatively, the user A can also preset the start and end of a vessel for the computer 9, thereby selecting an individual vessel section. In the last-mentioned case, if the selected vessel has a branch in the selected section, the section extending from the branch can be selected or not selected depending on the embodiment of the method according to the invention.

In the step S22, the computer 9 specifies a surrounding region 20, taking as a starting point the selected vessels. For example, the computer 9 can let the selected vessels in the volume data record 14 "grow"; see FIG. 11. The extent of the growth can be identical for all selected, e.g. a growth of a millimeter or a centimeter. However, it can also be dependent on the local thickness of the selected vessels, e.g. be 200% of the thickness. Ways for determining the surrounding region 20 are generally known to a person skilled in the art. The computer 9 preferably executes the step S22 fully automatically.

Taking the surrounding region 20 as a starting point, the computer 9 specifies the selected sub-volume 16 in the step S23, preferably fully automatically. For example (see FIG. 11 again), in a manner which is known per se, the computer 9 can determine the minimal convex envelope which fully contains the surrounding region 20. In this case, the convex envelope can correspond to the sub-volume 16.

FIG. 9 also shows a possible embodiment of the analysis method according to the invention, in which a step S26 in inserted between the steps S21 and S6. In the step S26, the computer 9 independently specifies a positioning of the recording arrangement 2. Depending on the application scenario, the positioning is specified e.g. such that the selected vessels overlap as little as possible and, to the greatest extent possible, run essentially parallel with the projection plane 18. Alternatively, the positioning of the recording arrangement 2 can be specified such that the sub-volume 16 is overlapped as little as possible by vessels. Methods for specifying suitable positionings of the recording arrangement 2 are known per se. The step S26 is preferably executed fully automatically by the computer 9. In the step S6, the recording arrangement 2 is moved to the positioning specified in the step 26, preferably semi-automatically or fully automatically.

If the examination object 8 was not moved between the capture of the projection images B', on the basis of which the volume data record 14 was determined, and the capture of the projection images B, which form the scenes of projection images B, it is possible exactly to specify the optimal positioning of the recording arrangement 2. The registration is also simpler in this case. For the purpose of positioning the recording arrangement 2, however, it is usually adequate if the implementation of the positioning is only optimal to a certain extent. A deviation of several degrees from the optimal positioning is generally tolerable.

It is also possible, but not essential, for the positioning of the recording arrangement 2, which positioning was determined by the computer 9, to be set automatically by the control device 9. It is sufficient for said positioning to be output to the user A of the radioscopy device 1, such that the user A can implement it in person, possibly specifying movement instructions to the control device 9.

Figure 12:
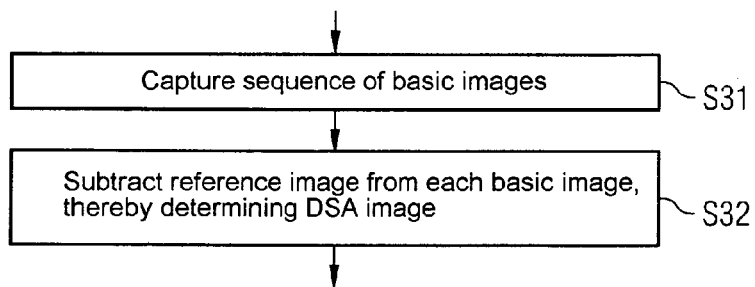
FIG. 12 shows a flow diagram.

In the context of the above explanations, it has been assumed that the projection images B are native images. This is indeed possible. However, the use of DSA images is preferred. In this case, the step S7 in FIG. 2 must be formulated in accordance with FIG. 12 as follows:

In accordance with FIG. 12, a sequence of basic images is captured in a step S31. The basic images are native images. In a step S32, a reference image is subtracted from each basic image, thereby determining a DSA image. The reference image is likewise a native image. It can be one of the basic images and specified uniformly for all other basic images (DSA in the conventional sense). Alternatively, however, it is possible separately to specify the reference images individually for each basic image, e.g. if dual-energy images are captured. The last-mentioned approach is particularly preferred if the examination object 8 is a moving examination object, e.g. a beating heart.

In the case of an examination object 8 which moves periodically—a beating heart can again be cited as an example—it is furthermore alternatively possible to provide for a prospective triggering in the case of the capture of the projection images B, B' or a retrospective selection from captured projection images B, B', in order to utilize only equiphase projection images B, B' of the examination object 8. Furthermore, the volume data record 14 must also show the examination object 8 in the correct phase position in this case.

By means of the analysis method according to the invention, and the associated program-based and device-based objects, a correct quantitative analysis of two-dimensional projection images B is possible for the first time. This approach the therefore particularly advantageous because it is significantly faster than the data acquisition for three-dimensional volume data records, requires a significantly smaller radiation dose, and is possible by means of angiography systems. The analysis method according to the invention is also not restricted to applications in the field of medicine, although this will be the most frequent application.

The above description serves exclusively to explain the present invention. The scope of the protection of the present invention shall be specified exclusively by the attached claims.

The invention claimed is:

1. An analysis method for data of an examination object, selecting a sub-volume of a volume data record,
   the data comprising at least one volume data record of the examination object and a plurality of two-dimensional projection images of the examination object, the volume data record includes a plurality of voxels and each voxel is assigned to a location in the three-dimensional space;

registering a plurality of projection images in relation to the volume data record, each projection image includes a multiplicity of pixels, each pixel is assigned to a location in a two-dimensional projection plane and has a pixel data value, and a projection volume is assigned to each pixel, each of the projection volumes are specified in that they are mapped by the radioscopy onto the pixels to which they are assigned; and specifying a functional parameter of the examination object for the pixels of the projection images depending on the pixel data values, wherein for each pixel, when specifying the functional parameter, consideration is given to the locations and the number of those which lie both within a sub-volume and within the projection volume that is assigned to the pixel concerned, and wherein the sub-volume is specified on the basis of the selected segmented vessels.

2. The analysis method as claimed in claim 1, wherein the examination object includes a vascular system with vessels and its surroundings, that the vascular system is segmented in the volume data record, that some of the segmented vessels are selected.

3. The analysis method as claimed in claim 2, wherein the projection images are captured following the selection of the segmented vessels, and that a positioning of a recording arrangement to capture the projection images is specified depending on which of the segmented vessels were selected.

4. The analysis method as claimed in claim 1, wherein the examination object includes a vascular system with vessels and its surroundings, that at least locations of segmented vessels are specified in the projection images, and that, based on the pixel data values of pixels which correspond to the segmented vessels, a standard influence factor is determined for all pixels of the projection images, which factor is included in the specification of the at least one functional parameter.

5. The analysis method as claimed in claim 1, wherein the examination object includes a vascular system with vessels and its surroundings, that at least locations of segmented vessels are specified in the projection images, and that the pixels which correspond to the segmented vessels are not taken into consideration when specifying the at least one functional parameter.

6. The analysis method as claimed in claim 5, Wherein, based on the pixel data values of pixels which correspond to the segmented vessels, a standard influence factor is determined for all pixels of the projection images, which factor is included in the specification of the at least one functional parameter.

7. The analysis method as claimed in claim 6, wherein that the vascular system is segmented in the volume data record, that some of the segmented vessels are selected, and that the sub-volume is specified on the basis of the selected segmented vessels.

8. The analysis method as claimed in claim 7, wherein the projection images are captured following the selection of the segmented vessels, and that a positioning of a recording arrangement to capture the projection images is specified depending on which of the segmented vessels were selected.

9. The analysis method as claimed in claim 1, wherein each projection image is determined as a DSA image of a corresponding basic image and a reference image.

10. The analysis method as claimed in claim 1, wherein the volume data record is determined based on a number of further projection images, and that the projection images and the further projection images are captured via the same recording arrangement.

11. A computer program encoded with a computer readable medium which comprises a sequence of machine instructions and causes a computer to execute an analysis method when it runs the sequence of machine instructions, the analysis method when executed comprising:

selecting a sub-volume of a volume data record, the data comprising at least one volume data record of the examination object and a plurality of two-dimensional projection images of the examination object, the volume data record includes a plurality of voxels and each voxel is assigned to a location in the three-dimensional space;

registering a plurality of projection images in relation to the volume data record, each projection image includes a multiplicity of pixels, each pixel is assigned to a location in a two-dimensional projection plane and has a pixel data value, and a projection volume is assigned to each pixel, each of the projection volumes are specified in that they are mapped by the radioscopy onto the pixels to which they are assigned; and specifying a functional parameter of the examination object for the pixels of the projection images depending on the pixel data values, wherein for each pixel, when specifying the functional parameter, consideration is given to the locations and the number of those which lie both within a sub-volume and within the projection volume that is assigned to the pixel concerned, and wherein the sub-volume is specified on the basis of the selected segmented vessels.

* * * * *